United States Patent
Muramatsu et al.

(10) Patent No.: US 6,472,581 B1
(45) Date of Patent: Oct. 29, 2002

(54) SILICONE SHEET AND SURGICAL BANDAGE MANUFACTURED USING THE SAME

(75) Inventors: Hiroshi Muramatsu; Masaya Fujimoto, both of Tokyo (JP)

(73) Assignee: Fujiyakuhin Co., Ltd., Omiya (JP)

( * ) Notice: Subject to any disclaimer, the term of this patent is extended or adjusted under 35 U.S.C. 154(b) by 0 days.

(21) Appl. No.: 09/700,753

(22) PCT Filed: May 13, 1999

(86) PCT No.: PCT/JP99/02479

§ 371 (c)(1),
(2), (4) Date: Nov. 20, 2000

(87) PCT Pub. No.: WO99/59816

PCT Pub. Date: Nov. 25, 1999

(30) Foreign Application Priority Data

May 18, 1998 (JP) .......................................... 10-134923

(51) Int. Cl.⁷ ................................................. A61F 13/00
(52) U.S. Cl. ............................. 602/41; 602/42; 602/48; 602/52; 602/900
(58) Field of Search .................. 602/41–48, 50–52, 602/900

(56) References Cited

U.S. PATENT DOCUMENTS 4,991,574 A * 2/1991 Pocknell ...................... 602/48

FOREIGN PATENT DOCUMENTS

| JP | 1-34370 | 2/1989 |
| JP | 5-69512 | 3/1993 |
| JP | 9-207275 | 8/1997 |

* cited by examiner

*Primary Examiner*—Michael A. Brown
*Assistant Examiner*—Lalita M Hamilton
(74) *Attorney, Agent, or Firm*—Oblon, Spivak, McClelland, Maier & Neustadt, P.C.

(57) ABSTRACT

The present invention relates to a silicone sheet obtained by integrally forming a silicone gel layer with a silicone elastomer layer to have a continuous heterogeneous structure, a surgical dressing using it and a manufacturing process of the sheet.

The dressing according to the present invention exhibits excellent adhesion, protective properties and conformity when applied to the affected part and has excellent physical strength as a whole so that it can be manufactured efficiently and can be handled readily.

19 Claims, 1 Drawing Sheet

PRODUCT OF POCKNELL

PRODUCT OF THE PRESENT INVENTION

PRODUCT OF POCKNELL

PRODUCT OF THE PRESENT INVENTION

SILICONE SHEET AND SURGICAL BANDAGE MANUFACTURED USING THE SAME

TECHNICAL FIELD

The present invention relates to a silicone sheet exhibiting excellent adhesion, protective properties and conformity when applied to the affected part and also excellent physical strength; and a surgical dressing made using the silicone sheet and a manufacturing process thereof.

BACKGROUND ART

A surgical dressing serves to protect the skin suffering from a burn or another injury such as traumatic injury, thereby promoting its recovery. Among various surgical dressings, a pressure dressing has been used widely for the treatment of hypertrophic scar, keloid or the like with a view not to disturbing the function of the affected part, for example, joint movement while completely protecting it from the outside world. This pressure dressing is however accompanied with such a drawback that it is not conformable to the joint movement or the like of patients, thereby impairing their moving function. In "Burns, Vol. 9, pages 201–204", described is the use of a silicone gel which can adapt and adhere itself readily to the contours of the human body.

Although such a silicone gel has strong adhesion and good conformity, its stickiness impairs handling properties and in addition, owing to weak physical strength, it is easily torn when formed into a sheet. It has been proposed in Japanese Patent Application Laid-Open No. Hei 3-75055 to improve this physical strength by using a woven cloth, nonwoven cloth or film for the inside or one side of the gel sheet as a reinforcing agent. Use of a film or nonwoven cloth however markedly impairs the preferable conformity of the silicone gel sheet, while a crepe gauze does not exhibit sufficient reinforcing power and its conformity is not satisfactory. In Japanese Patent Application Laid-Open No. Hei 1-34370, proposed is a laminate of a silicone gel sheet and a silicon elastomer. This laminate overcomes the above-described drawbacks to some extent, but not sufficiently. In addition, this proposal needs an extra step for forming the silicone elastomer into a sheet or film by calendering or the like prior to laminating with the silicone gel sheet. It is difficult to form this silicone elastomer film to have a thickness of 0.1 mm or less owing to limitations upon processing, which disturbs the production of a laminated sheet having satisfactory conformity.

An object of the present invention is therefore to provide a surgical dressing which is made using a silicone gel sheet having improved physical strength without losing its original excellence in adhesion, protective properties of the affected part and conformity thereto; is readily handled; and is excellent in the prevention or treatment of skin troubles or diseases.

DISCLOSURE OF THE INVENTION

Figure 1A:
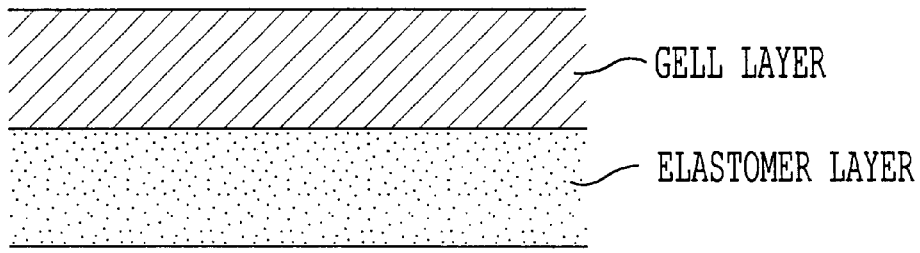
FIG. 1A describes the product of Pocknell, U.S. Pat. No. 4,991,574.
Figure 1B:
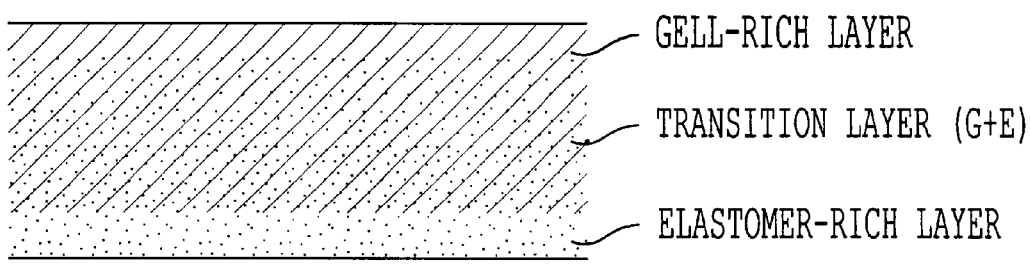
FIG. 1B shows a product of the present invention.

As a result of various investigations, the present inventors have found that a silicone sheet which exhibits excellent properties of a silicone gel on a wound facing surface but is free from tackiness on the other surface, is readily handled, and has reinforced physical strength as a whole and is therefore useful as a surgical dressing is available by integrally forming a silicone gel layer with a silicone elastomer layer to impart the interface therebetween with a continuous heterogeneous structure, leading to the completion of the present invention.

In the present invention, there are thus provided a silicone sheet obtained by integrally forming a silicone gel layer with a silicone elastomer layer to have a continuous heterogeneous structure, a surgical dressing made of the sheet; and a manufacturing process thereof.

The term "silicone gel" as used herein means a cured silicone gel composed mainly of organopolysiloxane, having a low crosslinking density and having a penetration of 10 or greater (usually, about 10 to 200) as measured by JIS K 2220 or ASTM D1403 (¼-scale cone). Such a silicone gel has hardness (rubber hardness) of 0 as measured by JIS K6301 and it corresponds to that having so low hardness (in other words, it is soft) as not to exhibit effective rubber hardness. The term "silicone elastomer" as used herein means a cured rubbery silicone gel (elastic body) having a higher crosslinking density than the silicone gel, is composed mainly of organopolysiloxane, and exhibits effective rubber hardness (>0) as measured by JIS K6301. The terms "silicone gel composition" and "silicone gel elastomer" as used herein mean uncured (prior to curing) compositions which will provide the above-described silicone gel and silicone elastomer by curing, respectively.

BEST MODE FOR CARRYING OUT THE INVENTION

The silicone sheet according to the present invention comprises a silicone gel layer and a silicone elastomer layer and has a continuous heterogeneous structure at their interface. This continuous heterogeneous structure can be formed by continuously changing the curing degree (crosslinking density) of the interface between the silicon gel layer which is composed of a polyorganosiloxane layer having a relatively low curing degree (crosslinking density) and the silicone elastomer layer which is composed of a polyorganosiloxane layer having a relatively high curing degree (crosslinking density). More preferably, the silicone sheet according to the present invention is composed mainly of a silicone gel sheet and has a silicone elastomer film formed on one side of this sheet. With a gradual increase in the crosslinking density, the interface between the sheet and the film acquires a continuous heterogeneous structure from a gel to an elastomer. Upon use of the silicone sheet of the present invention as a surgical dressing, the silicon gel layer is applied to the skin.

In the present invention, it is preferred that the silicone gel layer is formed by curing an addition reaction curing type silicone gel composition, while the silicone elastomer layer is formed by adding a silicone crosslinking agent to an addition reaction type curing type silicone gel composition, which is also usable for the formation of the silicone gel layer, and then curing the resulting silicone elastomer composition to raise its crosslinking density. The addition reaction curing type silicone gel composition for the formation of the silicone gel layer may differ from the addition reaction curing type silicone gel composition for the formation of the silicone elastomer layer, but an addition reaction curing type silicone elastomer composition available by adding a silicone crosslinking agent to the addition reaction curing type silicone gel composition used for the formation of the silicone gel layer is preferably used.

As the addition reaction curing type silicone gel composition, preferred are those each of which is composed mainly of (i) polyorganosiloxane having, in one molecule thereof, at least 0.5 silicon-bonded alkenyl group on average, (ii) polyorganohydrogensiloxane having, in one molecule thereof, at least two silicon-bonded hydrogen atoms (with the proviso that the total number of the alkenyl group and the silicon-bonded hydrogen atoms are 5 or greater), and (iii) an addition reaction catalyst and in which relative to one alkenyl group in the component (i), silicon-bonded hydrogen atoms in the component (ii) is incorporated to give its number of 0.5 to 0.98.

More preferred examples of the addition reaction curing type silicone gel composition include those comprising the following components (A) to (D):

(A) an alkenyl-containing polyorganosiloxane represented by the following mean composition formula:

$$R^1_a SiO_{(4-a)/2}$$

(wherein, $R^1$ represent a substituted or unsubstituted monovalent hydrocarbon group with the proviso that some of $R^1$s are alkenyl groups, and a stands for 1.85 to 2.4.) The alkenyl group is a functional group contributing to crosslinking reaction and it should be added in an amount of 0.001 mol % to 1.00 mol % relative to the silicon atom in one molecule.

(B) polyhydrogensiloxane represented by the following mean composition formula:

$$R^2_b H_c SiO_{(4-b-c)/2}$$

(wherein, $R^2$ represents a substituted or unsubstituted monovalent hydrocarbon group which is free of an aliphatic unsaturated bond, b stands for 0.7 to 2.2, c stands for 0.01 to 1.2 and at the same time, b and c satisfy the following equation: b+c=1 to 2.5.

The SiH group (that is, a silicon-bonded hydrogen atom) in the component (B) is added in an amount of 0.5 to 0.98 relative to 1 mole of the alkenyl group in the composition.

(C) 0.1 to 1000 ppm of a hydrosilylating reaction catalyst composed of platinum or a platinum compound.

(D) 0 to 50 parts by weight of an addition reaction inhibitor.

No particular limitation is imposed on the alkenyl group contained in $R^1$ insofar as it has a polymerizable vinyl group. Examples include lower alkenyl groups having about 2 to 4 carbon atoms, such as vinyl, allyl, propenyl and butenyl. Among them, a vinyl group is preferred. Examples of the substituted or unsubstituted hydrocarbon group represented by $R^1$ other than the alkenyl group include alkyl groups such as methyl, ethyl, propyl, butyl, hexyl, cyclohexyl and octyl, aryl groups such as phenyl, tolyl and xylyl, aralkyl groups such as benzyl and phenylethyl, and halogen-substituted alkyl groups such as chloromethyl and trifluoropropyl obtained by substituting some of the hydrogen atoms bonded to the carbon atom of the above-described groups with the corresponding number of halogen atoms. Among them, alkyl groups having about 1 to 6 carbon atoms and a phenyl group are preferred, with the methyl group being particularly preferred.

As the substituted or unsubstituted monovalent hydrocarbon group represented by $R^2$, those exemplified above as the group other than the alkenyl group can be mentioned. Preferred are alkyl groups having about 1 to 6 carbon atoms, and a phenyl group, with a methyl group being particularly preferred.

As the hydrosilylating reaction catalyst as the component (C) composed of platinum or a platinum compound, those conventionally known can be used. Examples include chloroplatinic acid and platinum chloride, and various complexes derived therefrom.

Examples include platinum black, chloroplatinic acid, alcohol-modified chloroplatinic acid, and complexes of chloroplatinic acid with an olefin, an aldehyde, vinyl siloxane or an acetylene alcohol, of which the platinum complex of vinyl siloxane is preferably used. The catalyst is added, as a platinum metal, in an amount of 0.1 to 1000 ppm relative to the total amount of the components (A) and (B). At amounts of the platinum metal less than 0.1 ppm of the total amount of the components (A) and (B), curing reaction does not proceed sufficiently. Amounts exceeding 1000 ppm are, on the other hand, economically disadvantageous.

As the component (D), an addition reaction inhibitor selected from the group consisting of a vinyl-containing organopolysiloxane, acetylene alcohols, triallyl isocyanurates, alkyl maleates, hydroperoxide, tetramethylethylene diamine and benzotriazole, and mixtures thereof may be added in an amount not exceeding 50 parts.

The silicone sheet according to the present invention can be prepared, for example, by forming an addition reaction curing type silicone gel composition (composition to be a silicone gel) into a sheet, applying or spraying a silicone crosslinking agent onto the resulting sheet after or before curing and then curing. Alternatively, it can be prepared by spreading an addition reaction curing type silicone elastomer composition (a composition to be a silicone elastomer) into a thin film, pouring an addition reaction curing silicone gel composition (a composition to be a silicone gel) over the thin film without curing to form the corresponding sheet and then curing both components simultaneously.

In the above-described process, the silicone crosslinking agent may be diluted with any solvent.

In the above-described process, the silicon crosslinking agent can be applied by a brush, while spraying can be conducted by an ordinarily-employed sprayer. At the part to which the silicone crosslinking agent is applied or sprayed, a silicone elastomer composition to be cured into the corresponding silicone elastomer is produced. Then, curing is effected by heating or allowing it to stand, whereby a sheet having a continuous heterogeneous structure is available. In the latter process, the addition reaction curing type silicone gel composition is preferably poured so as to be overlapped over the surface of the thin film of the addition reaction curing type silicone elastomer composition.

In the above-described processes, simultaneous curing of the silicone elastomer composition and silicone gel composition is preferred, because the boundary between these two compositions disappear during curing and the cured product thus obtained is able to acquire a continuous heterogeneous structure. In addition, use of a transparent or semi-transparent silicone elastomer composition is preferred, because the affected part can be observed through it well when it is clinically applied as a surgical dressing.

The sheet according to the present invention can be manufactured simply and specifically by pouring a silicone elastomer composition into a PET tray, pouring thereinto a silicone gel composition without curing the silicone elastomer composition, curing both of them by heating in a hot-air circulating oven or the like, taking the cured product out of the oven and packing it while covering the upper gel surface with a separator such as polyethylene film.

The silicon gel layer of the silicone sheet thus obtained according to the present invention preferably has, as an index of hardness, a penetration of at least 10, particularly 20 to 200 as defined in JIS K2220 or ASTM D1403 (¼-scale cone). At a penetration less than 10, the resulting sheet lacks in adhesion and shape conformity. At a penetration exceeding 200, on the other hand, the silicon gel layer becomes too soft, which makes it difficult to handle the resulting gel. The silicone gel layer of the sheet according to the present invention usually has adhesion, but no particular limitation is imposed on its adhesion. The silicon elastomer layer, on the other hand, is free from adhesion or if any, has markedly low adhesion.

Since the sheet of the present invention has, on one side thereof, a silicone gel layer and therefore is excellent in adhesion to an uneven surface, it can be used for various purposes which need such adhesion. Above all, use as a surgical dressing is preferred. Upon use as a surgical dressing, it is preferred to peel a releasable material, which has been adhered in advance onto the gel surface, just before use. Examples of the releasable material include films of an organic resin such as fluorine resin, polyethylene, polypropylene or polyester, paper covered with such an organic resin and fluorosilicone-treated film/paper.

Although no particular limitation is imposed on the size of a surgical dressing made of the sheet of the present invention, it preferably has a thickness of 1 mm to 5 mm from the viewpoint of handling ease as a surgical dressing.

EXAMPLES

The present invention will hereinafter be described more specifically by Examples. It should however be borne in mind that the present invention is not limited to or by them.

Example 1

Polydimethylsiloxane (100 g) blocked at both ends thereof with a dimethylvinylsiloxy group and having a viscosity at 25° C. of 1000 cS, 5.5 g of polydimethylsiloxane having an average polymerization degree of 30, blocked at both ends thereof with a trimethylsilyl group, and containing three methylhydrogensiloxane units, and a vinyl-containing siloxane complex derived from chloroplatinic acid were mixed to give a platinum concentration of 10 ppm. The resulting mixture was spread over a polyethylene film to form a sheet of 5 mm thick. Prior to curing, polyorganohydrogensiloxane having an average polymerization degree of 12, and containing, in one molecule thereof, 10 silicon-bonded hydrogen atoms as a methylhydrogensiloxane unit was sprayed to the sheet, followed by curing at 80° C. for 30 minutes, whereby a gel sheet having on the upper surface thereof a silicone elastomer layer was obtained. The resulting sheet had a silicone elastomer formed thereon so that it became a silicone gel dressing easy in removal from the polyethylene film and handling as a dressing, and having excellent conformity to the affected part.

Example 2

Polydimethylsiloxane (100 g) blocked at both ends thereof with a dimethylvinylsiloxy group and having a viscosity at 25° C. of 1000 cS, 5.5 g of polydimethylsiloxane having an average polymerization degree of 30, blocked at both ends thereof with a trimethylsilyl group and containing three methylhydrogensiloxane units, and a vinyl-containing siloxane complex derived from chloroplatinic acid were mixed to give a platinum concentration of 10 ppm. The resulting mixture was spread over a polyethylene film to form a sheet of 5 mm thick. Prior to curing, a 10% hexane solution of polyorganohydrogensiloxane having an average polymerization degree of 12, and containing, in one molecule thereof, 10 silicon-bonded hydrogen atoms as a methylhydrogensiloxane unit was sprayed to the sheet, followed by curing at 80° C. for 30 minutes, whereby a gel sheet having on the upper surface thereof a silicone elastomer layer was obtained. The resulting sheet had a silicone elastomer formed thereon so that it became a silicone gel dressing easy in removal from the polyethylene film and handling as a dressing, and having excellent conformity to the affected part.

Example 3

Polydimethylsiloxane (94 g) blocked at both ends thereof with a dimethylvinylsiloxy group and having a viscosity at 25° C. of 1000 cS, 0.4 g of polydimethylsiloxane having an average polymerization degree of 90, blocked at both ends thereof with a trimethylsilyl group and containing 30 methylhydrogensiloxane units, 5.0 g of polydimethylsiloxane having an average polymerization degree of 20 and blocked at both ends thereof with a dimethylhydrogensiloxy group, and a vinyl-containing siloxane complex derived from chloroplatinic acid were mixed to give a platinum concentration of 10 ppm. The resulting mixture was spread over a polyethylene film to form a sheet of 5 mm thick. Prior to curing, a 10% hexane solution of polyorganohydrogensiloxane having an average polymerization degree of 12, and containing, in one molecule thereof, 10 silicon-bonded hydrogen atoms as a methylhydrogensiloxane unit was sprayed to the sheet, followed by curing at 80° C. for 15 minutes, whereby a gel sheet having on the upper surface thereof a silicone elastomer layer was obtained. The resulting sheet had a silicone elastomer formed thereon so that it became a silicone gel dressing easy in removal from the polyethylene film and handling as a dressing, having high tackiness and having excellent conformity to the affected part.

Example 4

Polydimethylsiloxane (83 g) blocked at both ends thereof with a dimethylvinylsiloxy group and having a viscosity at 25° C. of 1000 cS, 10 g of polydimethylsiloxane blocked, at one end thereof, with a dimethylvinylsiloxy group and, at the other end thereof, with a trimethylsilyl group on average and having a viscosity at 25° C. of 750 cS, 0.25 g of polydimethylsiloxane having an average polymerization degree of 90, blocked at both ends thereof with a trimethylsilyl group and containing 30 methylhydrogensiloxane units, 6.0 g of polydimethylsiloxane having an average polymerization degree of 20 and blocked at both ends thereof with a dimethylhydrogensiloxy group, and a vinyl-containing siloxane complex derived from chloroplatinic acid were mixed to give a platinum concentration of 10 ppm. The resulting mixture was spread over a polyethylene film to form a sheet of 5 mm thick. Prior to curing, a 10% hexane solution of polyorganohydrogensiloxane having an average polymerization degree of 12, and containing, in one molecule thereof, 10 silicon-bonded hydrogen atoms as a methylhydrogensiloxane unit was sprayed to the sheet, followed by curing at 80° C. for 30 minutes, whereby a gel sheet having on the upper surface thereof a silicone elastomer layer was obtained. The resulting sheet had a silicone elastomer formed thereon so that it became a silicone gel dressing easy in removal from the polyethylene film and handling as a dressing, having high tackiness and having excellent conformity to the affected part.

Example 5

Polydimethylsiloxane (100 g) blocked at both ends thereof with a dimethylvinylsiloxy group and having a viscosity at 25° C. of 1000 cS, 5.5 g of polydimethylsiloxane having an average polymerization degree of 30, blocked at both ends thereof with a trimethylsilyl group and containing three methylhydrogensiloxane units, and a vinyl-containing siloxane complex derived from chloroplatinic acid were mixed to give a platinum concentration of 10 ppm. The resulting mixture was spread over a polyethylene film to form a sheet of 5 mm thick, followed by curing to some extent by heating at 80° C. for 15 minutes.

Polyorganohydrogensiloxane having an average polymerization degree of 12 and containing, in one molecule thereof, 10 silicon-bonded hydrogen atoms as a methylhydrogensiloxane unit was applied to the resulting sheet by a brush, followed by curing at 80° C. for 30 minutes, whereby a gel sheet having on the upper surface thereof a silicone elastomer layer was obtained. The resulting sheet had a silicone elastomer formed thereon so that it became a silicone gel dressing easy in removal from the polyethylene film and handling as a dressing, and having excellent conformity to the affected part.

Example 6

Polydimethylsiloxane (100 g) blocked at both ends thereof with a dimethylvinylsiloxy group and having a viscosity at 25° C. of 1000 cS, 5.5 g of polydimethylsiloxane having an average polymerization degree of 30, blocked at both ends thereof with a trimethylsilyl group and containing three methylhydrogensiloxane units, and a vinyl-containing siloxane complex derived from chloroplatinic acid were mixed to give a platinum concentration of 10 ppm. The resulting mixture was spread over a polyethylene film to form a sheet of 5 mm thick, followed by curing by heating at 80° C. for 15 minutes until the resulting sheet lost its fluidity. Polyorganohydrogensiloxane having an average polymerization degree of 12 and containing, in one molecule thereof, 10 silicon-bonded hydrogen atoms as a methylhydrogensiloxane unit was applied to the resulting sheet by a brush, followed by allowing to stand for 24 hours for curing, whereby a gel sheet having on the upper surface thereof a silicone elastomer layer was obtained. The resulting sheet had a silicone elastomer formed thereon so that it became a silicone gel dressing easy in removal from the polyethylene film and handling as a dressing, and having excellent conformity to the affected part.

Example 7

Polydimethylsiloxane (100 g) blocked at both ends thereof with a dimethylvinylsiloxy group and having a viscosity at 25° C. of 30000 cS, 1.2 g of polydimethylsiloxane having an average polymerization degree of 90, blocked at both ends thereof with a trimethylsilyl group and containing 30 methylhydrogensiloxane units, 5.5 g of fumed silica having a dimethyldichlorosilane-treated surface area of 200 m$^2$/g, and a vinyl-containing siloxane complex derived from chloroplatinic acid were mixed to give a platinum concentration of 10 ppm. The resulting mixture was spread over a PET film as a thin film of 0.1 mm thick. Without curing it, a mixture obtained by mixing 100 g of polydimethylsiloxane blocked at both ends thereof with a dimethylvinylsiloxy group and having a viscosity at 25° C. of 1000 cS, 5.5 g of polydimethylsiloxane having an average polymerization degree of 30, blocked at both ends thereof with a trimethylsilyl group and containing three methylhydrogensiloxane units, and a vinyl-containing siloxane complex derived from chloroplatinic acid to give a platinum concentration of 10 ppm was poured onto the resulting thin film, whereby a sheet of 5 mm thick as a whole was obtained. Simultaneous curing of them at 80° C. for 30 minutes yielded a gel/elastomer sheet having a continuous heterogeneous structure. The resulting sheet had, on the bottom surface thereof, a silicone elastomer having excellent elongation and, on the upper surface, a tacky gel surface formed, so that it became a silicone gel dressing easily handled as a dressing and having excellent conformity to the affected part.

Example 8

Polydimethylsiloxane (100 g) blocked at both ends thereof with a dimethylvinylsiloxy group and having a viscosity at 25° C. of 30000 cS, 1.2 g of polydimethylsiloxane having an average polymerization degree of 90, blocked at both ends thereof with a trimethylsilyl group and containing 30 methylhydrogensiloxane units, 5.5 g of fumed silica having a dimethyldichlorosilane-treated surface area of 200 m$^2$/g, and a vinyl-containing siloxane complex derived from chloroplatinic acid were mixed to give a platinum concentration of 10 ppm. The resulting mixture was spread in a PET tray of 6 mm deep to form a thin film of 0.1 mm thick. Without curing the resulting mixture in the form of a thin film, a mixture obtained by mixing 100 g of polydimethylsiloxane blocked at both ends thereof with a dimethylvinylsiloxy group and having a viscosity at 25° C. of 1000 cS, 5.5 g of polydimethylsiloxane having an average polymerization degree of 30, blocked at both ends thereof with a trimethylsilyl group and containing three methylhydrogensiloxane units, and a vinyl-containing siloxane complex derived from chloroplatinic acid to give a platinum concentration of 10 ppm was poured onto the thin film and spread like a sheet having a thickness of 5 mm as a whole. Simultaneous curing of them at 80° C. for 30 minutes yielded a gel/elastomer sheet having a continuous heterogeneous structure. Over the gel surface, an embossed polyethylene film was stacked as a separator and the peripheral part of the film was heat sealed to pack the sheet. The resulting sheet had, on the bottom surface thereof, a silicone elastomer having excellent elongation and, on the upper surface, a tacky gel surface formed and was hermetically sealed until just before use so that it became a silicone gel dressing which was sanitary, easily handled as a dressing, and had excellent conformity to the affected part.

Example 9

Liquid 1 was prepared by weighing, as a silicone elastomer layer, KE1300T (Shin'etsu Chemical), RTV thinner and CS-32-1664 (Shin'etsu Chemical) at a ratio of 10:3:1.5 and uniformly mixing them. The resulting Liquid 1 was uniformly applied to the bottom and side surfaces of a PP container of 1 cm deep.

Liquid 2 was, on the other hand, prepared by weighing, as a silicone gel layer, KE1051A (Shin'etsu Chemical), and KE1051B (Shin'etsu Chemical) at a ratio of 1:1 and uniformly mixing them. The resulting Liquid 2 was weighed in an amount of 8.75 times the amount of Liquid 1 and poured in the PP container coated with Liquid 1, followed by curing at 80° C. for 2 hours to manufacture a silicone gel sheet which was tacky only on the upper surface, was free from tackiness on the bottom and side surfaces contiguous to the container and was able to be put on the market as was after covered with a lid or sealed.

Comparative Example 1

Polydimethylsiloxane (100 g) blocked at both ends thereof with a dimethylvinylsiloxy group and having a viscosity at 25° C. of 1000 cS, 5.5 g of polydimethylsiloxane having an average polymerization degree of 30, blocked at both ends thereof with a trimethylsilyl group and containing three methylhydrogensiloxane units, and a vinyl-containing siloxane complex derived from chloroplatinic acid were mixed to give a platinum concentration of 10 ppm. The resulting mixture was spread over a polyethylene film to form a sheet of 5 mm thick, followed by curing at 80° C. for 15 minutes, whereby a gel sheet was obtained. Since the gel sheet had on the upper surface thereof no silicone elastomer formed, it was inferior in handling as a dressing and was torn during the treatment work.

Comparative Example 2

Polydimethylsiloxane (100 g) blocked at both ends thereof with a dimethylvinylsiloxy group and having a viscosity at 25° C. of 1000 cS, 5.5 g of polydimethylsiloxane having an average polymerization degree of 30, having at both ends thereof with a trimethylsilyl group and containing three methylhydrogensiloxane units, and a vinyl-containing siloxane complex derived from chloroplatinic acid were mixed to give a platinum concentration of 10 ppm. The resulting mixture was spread in a nonwoven-fabric-laid container to form a sheet of 5 mm thick, followed by curing at 80° C. for 30 minutes, whereby a gel sheet was obtained. Having the bottom surface reinforced with the non-woven fabric, the resulting sheet was easy to handle, but was not satisfactory as a silicone gel dressing because of inferiority in conformity to the affected part.

Industrial Applicability

The silicone sheet according to the present invention exhibits excellent adhesion, protective properties and conformity when applied to the affected part and has excellent physical strength as a whole so that it is useful as a surgical dressing which can be manufactured efficiently, and can be handled markedly easily.

What is claimed is:

1. A silicone sheet, which comprises an integrally formed silicone gel layer with a silicone elastomer layer, thereby having a continuous heterogeneous structure, which silicone sheet is produced by a process comprising:
   a) spreading an addition reaction curing silicone elastomer composition into a thin film;
   b) pouring an addition reaction curing silicone gel composition onto said thin film without curing; and
   c) curing said elastomer composition and gel composition simultaneously.

2. The silicone sheet of claim 1, wherein in the process of producing the same, said addition reaction curing silicone gel composition comprises mainly (i) polyorganosiloxane having, in one molecule thereof, at least 0.5 silicon-bonded alkenyl groups on average, (ii) polyorganohydrogensiloxane having, in one molecule thereof, at least 2 silicone-bonded hydrogen atoms, with the proviso that a total number of the above-described alkenyl groups and the silicon-bonded hydrogen atoms is at least 5, and (iii) an addition reaction catalyst, and in which said silicon-bonded hydrogen atom in the component (ii) is incorporated to give a number of 0.5 to 0.98 relative to one alkenyl group in the component.

3. A surgical dressing, comprising the silicone sheet of claim 2.

4. The surgical dressing of claim 3, having a thickness of from about 1 to 5 mm.

5. The silicone sheet of claim 1, wherein said addition reaction curing silicone gel composition comprises an alkenyl-containing polyorganosiloxane.

6. The silicone sheet of claim 5, wherein said alkenyl-containing polyorganosiloxane has the formula:

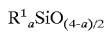

wherein:
   $R^1$ is an optionally substituted monovalent hydrocarbon group, wherein at least some $R^1$ are alkenyl; and
   a is 1.85 to 2.4.

7. The silicone sheet of claim 6, wherein said formula $R^1_a SiO_{(4-a)/2}$, $R^1$ is $C_2$–$C_4$ alkenyl.

8. The silicone sheet of claim 7, wherein said $R^1$ is vinyl.

9. The silicone sheet of claim 8, wherein said remaining $R^1$ groups comprise alkyl, aryl, aralkyl or haloalkyl groups.

10. The silicone sheet of claim 9, wherein said remaining $R^1$ groups comprise $C_1$–$C_6$ alkyl or phenyl.

11. The silicone sheet of claim 10, wherein said remaining $R^1$ groups comprise $C_1$–$C_6$ alkyl, which is methyl.

12. The silicone sheet of claim 1, wherein said addition reaction curing silicone gel composition comprises a polyhydrogen siloxane having the formula:

wherein:
   $R^2$ is an optionally substituted monovalent hydrocarbon group free of an aliphatic unsaturated bond;
   b is 0.7 to 2.2;
   c is 0.01 to 1.2; and
   (b+c)=1 to 2.5.

13. A surgical dressing, comprising the silicone sheet of claim 1.

14. The surgical dressing of claim 13, having a thickness of from about 1 to 5 mm.

15. A process for producing the silicone sheet of claim 1, which comprises the steps of:
   a) spreading an addition reaction curing silicone elastomer composition into a thin film;
   b) pouring an addition reaction curing type silicone gel composition onto the thin film without curing; and
   c) curing the elastomer composition and gel composition simultaneously.

16. The process of claim 15, wherein said addition reaction curing silicone gel composition comprises mainly (i) polyorganosiloxane having, in one molecule thereof, at least 0.5 silicon-bonded lower alkenyl group on average, (ii) polyorganohydrogensiloxane having, in one molecule thereof, at least 2 silicon-bonded hydrogen atoms with the proviso that the total number of the above-described alkenyl group and the silicon-bonded hydrogen atoms is at least 5), and (iii) an addition reaction catalyst and in which said silicon-bonded hydrogen atom in the component (ii) is incorporated to give a number of 0.5 to 0.98 relative to one alkenyl group in the component (i); and said silicone crosslinking agent being polyorganohydrogensiloxane containing, in one molecule thereof, at least 3 silicon-bonded hydrogen atoms.

17. A silicone sheet, comprising an integrally formed silicone gel layer with a silicone elastomer layer, thereby having a continuous heterogeneous structure, wherein the silicone gel layer is formed by curing an addition reaction curing silicone gel composition which is composed mainly of (i) polyorganosiloxane having, in one molecule thereof, at least 0.5 silicon-bonded alkenyl groups on average, (ii) polyorganohydrogensiloxane having, in one molecule thereof, at least 2 silicone-bonded hydrogen atoms, with the proviso that a total number of the above-described alkenyl groups and the silicon-bonded hydrogen atoms is at least 5, and (iii) an addition reaction catalyst, and in which the silicon-bonded hydrogen atom in the component (ii) is incorporated to give a number of 0.5 to 0.98 relative to one alkenyl group in component (i).

18. The silicone sheet of claim 17, wherein said silicone elastomer layer is formed by curing a silicone elastomer composition obtained by adding a silicone crosslinking compound to an addition reaction curing silicone gel composition.

19. The silicone sheet of claim 18, wherein said silicone crosslinking agent is a polyorganohydrogensiloxane having, in one molecule thereof, at least 3 silicon-bonded hydrogen atoms.

* * * * *